(12) United States Patent
Mallard

(10) Patent No.: US 8,952,066 B2
(45) Date of Patent: *Feb. 10, 2015

(54) PHARMACEUTICAL/COSMETIC, E.G., ANTI-ACNE COMPOSITIONS COMPRISING AT LEAST ONE NAPHTHOIC ACID COMPOUND, BENZOYL PEROXIDE AND AT LEAST ONE FILM-FORMING AGENT

(75) Inventor: Claire Mallard, Mougins (FR)

(73) Assignee: Galderma Research & Development, Biot (FR)

( * ) Notice: Subject to any disclaimer, the term of this patent is extended or adjusted under 35 U.S.C. 154(b) by 128 days.

This patent is subject to a terminal disclaimer.

(21) Appl. No.: 12/788,865

(22) Filed: May 27, 2010

(65) Prior Publication Data
US 2011/0135584 A1 Jun. 9, 2011

Related U.S. Application Data

(63) Continuation of application No. PCT/FR2008/052169, filed on Dec. 1, 2008.

(60) Provisional application No. 61/004,763, filed on Nov. 30, 2007.

(51) Int. Cl.

| | | |
|---|---|---|
| A61K 8/04 | (2006.01) |
| A61K 8/38 | (2006.01) |
| A61K 47/18 | (2006.01) |
| A61K 47/10 | (2006.01) |
| A61Q 19/00 | (2006.01) |
| A61K 31/327 | (2006.01) |
| A61K 31/192 | (2006.01) |
| A61K 8/368 | (2006.01) |
| A61K 8/81 | (2006.01) |
| A61K 47/44 | (2006.01) |
| A61Q 5/00 | (2006.01) |
| A61K 47/36 | (2006.01) |
| A61K 47/32 | (2006.01) |
| A61K 8/73 | (2006.01) |
| A61K 47/38 | (2006.01) |
| A61K 9/00 | (2006.01) |
| A61K 9/06 | (2006.01) |
| A61K 47/24 | (2006.01) |
| A61Q 19/08 | (2006.01) |
| A61K 47/14 | (2006.01) |

(52) U.S. Cl.
CPC ............... *A61K 9/0014* (2013.01); *A61K 8/38* (2013.01); *A61K 8/368* (2013.01); *A61K 47/10* (2013.01); *A61K 8/8135* (2013.01); *A61K 47/44* (2013.01); *A61Q 5/00* (2013.01); *A61K 8/8182* (2013.01); *A61Q 19/008* (2013.01); *A61K 47/36* (2013.01); *A61K 47/32* (2013.01); *A61K 8/735* (2013.01); *A61K 8/731* (2013.01); *A61K 47/38* (2013.01); *A61K 31/192* (2013.01); *A61Q 19/004* (2013.01); *A61K 9/06* (2013.01); *A61K 47/24* (2013.01); *A61K 31/327* (2013.01); *A61Q 19/08* (2013.01); *A61K 47/14* (2013.01)

USPC ........................... 514/569; 514/544; 514/714

(58) Field of Classification Search
None
See application file for complete search history.

(56) References Cited

U.S. PATENT DOCUMENTS

| | | | |
|---|---|---|---|
| 6,689,339 B1 | 2/2004 | Tanaka et al. | |
| 2003/0096012 A1* | 5/2003 | Besse et al. ................... | 424/489 |
| 2003/0170196 A1* | 9/2003 | Orsoni et al. ............... | 424/70.17 |
| 2004/0161402 A1* | 8/2004 | Brooks et al. ............... | 424/70.15 |

FOREIGN PATENT DOCUMENTS

| | | |
|---|---|---|
| CA | 2347907 A1 | 5/2000 |
| EP | 1967180 A1 | 9/2008 |
| JP | 2004217675 A | 8/2004 |
| JP | 2005515180 A | 5/2005 |
| WO | 03041680 A1 | 5/2003 |
| WO | 2007004201 A1 | 1/2007 |
| WO | WO 2007/002831 A2 | 1/2007 |
| WO | WO 2007/031883 A2 | 3/2007 |
| WO | WO 2008/006848 A1 | 1/2008 |
| WO | WO 2008/006888 A1 | 1/2008 |
| WO | WO 2008/017914 A2 | 2/2008 |
| WO | WO 2008/065306 A1 | 6/2008 |
| WO | WO 2008/087354 A2 | 7/2008 |
| WO | 2008107193 A1 | 9/2008 |

OTHER PUBLICATIONS

Korbut (Benzoyl peroxide, adapalene, and their combination in the treatment of acne vulgaris, 32 J. Dermatology 169 (2005).*
International Search Report corresponding to PCT/FR 2008/052169 mailed Sep. 22, 2009.
Korkut et al., "Benzoyl Peroxide, Adapalene and Their Combination in the Treatment of Acne Vulgaris", The Journal of Dermatology, 2005, pp. 169-173, vol. 32.
ANON, "Guide Vidal des medicaments", Editions du Vidal, 1997, p. 481.
Definition of "essential oil", *The Condensed Chemical Dictionary*, Tenth Edition, Ed. Gessner G. Hawley, Van Nostrand Reinhold Company, NY, NY, 1981, p. 418.

* cited by examiner

*Primary Examiner* — H. Sarah Park
(74) *Attorney, Agent, or Firm* — Dentons US LLP

(57) ABSTRACT

Stable pharmaceutical/cosmetic compositions for topical application, notably for the treatment of acne vulgaris include, formulated into a physiologically acceptable medium, at least one naphthoic acid compound, benzoyl peroxide and at least one film-forming agent, the at least one naphthoic acid compound and the benzoyl peroxide advantageously being in a dispersed form therein.

29 Claims, No Drawings

PHARMACEUTICAL/COSMETIC, E.G., ANTI-ACNE COMPOSITIONS COMPRISING AT LEAST ONE NAPHTHOIC ACID COMPOUND, BENZOYL PEROXIDE AND AT LEAST ONE FILM-FORMING AGENT

CROSS-REFERENCE TO EARLIER APPLICATIONS

This application is a continuation of PCT/FR 2008/052169, filed Dec. 1, 2008 and designating the United States (published in the French language on Jun. 25, 2009 as WO 2009/077693 A2; the title and abstract were also published in English), which claims benefit under 35 U.S.C. §119(e) of U.S. Provisional Application No. 61/004,763, filed Nov. 30, 2007, each hereby expressly incorporated by reference in its entirety and each assigned to the assignee hereof.

BACKGROUND OF THE INVENTION

1. Technical Field of the Invention

The present invention relates to compositions for topical application, to processes for preparing such compositions and to applications thereof as cosmetic or pharmaceutical products, the compositions being particularly useful for treating acne.

2. Description of Background and/or Related and/or Prior Art

Acne is a common multi-factor pathology that attacks skin rich in sebaceous glands (face, shoulder area, arms and intertriginous areas). It is the most commonly occurring form of dermatosis. The following five pathogenic factors play a determining role in the development of acne:
  1. genetic predisposition;
  2. overproduction of sebum (seborrhoea);
  3. androgens;
  4. follicular keratinization disorders (comedogenesis); and
  5. bacterial colonization and inflammatory factors.

There are several forms of acne, the common factor of all of them being attack of the pilosebaceous follicles. Exemplary are acne conglobata, acne keloid on the nape of the neck, acne medicamentosa, recurrent miliary acne, acne necrotica, acne neonatorum, premenstrual acne, occupational acne, acne rosacea, senile acne, solar acne and acne vulgaris.

Acne vulgaris, also known as polymorphous juvenile acne, is the most common. It comprises four stages, but it is not necessary to pass through all the stages:

Stage 1 corresponds to comedonal acne, characterized by a large number of open and/or closed comedones and of microcysts.

Stage 2, or papulopustular acne, is of mild to moderate seriousness. It is characterized by the presence of open and/or closed comedones and microcysts, but also of red papules and of pustules. It mainly affects the face and leaves few scars.

Stage 3, or papulocomedonal acne, is more serious and extends to the back, the thorax and the shoulders. It is accompanied by a larger number of scars.

Stage 4, or nodulocystic acne, is accompanied by numerous scars. It exhibits nodules and also has large painful purplish pustules.

The various forms of acne described above can be treated with active agents, such as antiseborrhoeics and antiinfectives, for example benzoyl peroxide (in particular, the product Eclaran® marketed by Pierre Fabre), with retinoids, such as tretinoin (in particular, the product Retacnyl® marketed by Galderma) or isotretinoin (the product Roaccutane® marketed by Laboratoires Roche), or with naphthoic acid compounds. Naphthoic acid compounds, such as, in particular, 6-[3-(1-adamantyl)-4-methoxyphenyl]-2-naphthoic acid, commonly known as adapalene (the product Differine® marketed by Galderma), are widely described and recognized as active ingredients which are as effective as tretinoin in the treatment of acne.

The combination of several local treatments (antibiotics, retinoids, peroxides, zinc) is also used in dermatology to increase the efficacy of the active ingredients and to reduce their toxicity (Cunliffe W. J., J. Dermatol. Treat., 2000, 11 (suppl. 2), S13-S14) but the multiple application of various dermatological products can be quite laborious and demanding for the patient.

The advantage of providing a new treatment which is effective under dermatological conditions, in a stable composition offering good cosmeticity, and which can be applied just once and is pleasant for the patient to use, is therefore apparent.

Among this panoply of therapeutics proposed to those skilled in the art, none would encourage one to combine, in the same composition, benzoyl peroxide and a retinoid.

However, the formulation of such a composition presents several problems.

First, the efficacy of benzoyl peroxide is linked to its decomposition when it is brought into contact with the skin. In fact, it is the oxidizing properties of the free radicals produced during this decomposition which result in the desired effect. Thus, to maintain optimum efficacy of the benzoyl peroxide, it is important to prevent it from decomposing before use, i.e., during storage.

However, benzoyl peroxide is an unstable chemical compound, which makes it difficult to formulate it into final products.

The solubility and stability of benzoyl peroxide have been studied by Chellquist et al. in ethanol, propylene glycol and various mixtures of polyethylene glycol 400 (PEG 400) and water (Chellquist E. M. and Gorman W. G., Pharm. Res., 1992, Vol. 9: 1341-1346).

This prior art specifies, moreover, that the stability of benzoyl peroxide is greatly influenced by the chemical composition of the formulation and by the storage temperature thereof. Benzoyl peroxide is extremely reactive and degrades in solution at low temperature due to the instability of its peroxide bond.

The authors thus note that benzoyl peroxide in solution degrades more or less rapidly in all of the solvents studied, depending on the type of solvent and on the concentration thereof.

The degradation times of benzoyl peroxide in PEG 400 (0.5 mg/g), in ethanol and in propylene glycol are, respectively, 1.4, 29 and 53 days at 40° C.

Such a degradation does not make it possible to formulate a product intended for sale.

Another difficulty to be overcome in the formulation of a composition comprising both benzoyl peroxide and a retinoid is that most retinoids are particularly sensitive to natural oxidation, to visible light and to ultraviolet radiation, and since benzoyl peroxide is a strong oxidizing agent, the chemical compatibility of these compounds in the same formulation poses numerous problems of stability from the physical and chemical point of view.

A study of the stability of two retinoids was carried out by combining two commercially available products, one containing a retinoid (tretinoin or adapalene) and the second being benzoyl peroxide-based (B. Martin et al., Br. J. Dermatol. (1998) 139 (suppl. 52), 8-11).

The presence of the benzoyl peroxide-based formulation causes very rapid degradation of the oxidation-sensitive retinoids: it is measured that 50% of the tretinoin degrades in 2 hours, and 95% in 24 hours. In the composition in which the retinoid is adapalene, no degradation of the adapalene was measured for 24 hours. This study confirms that benzoyl peroxide is degraded and degrades oxidation-sensitive retinoids over time, gradually releasing benzoic acid into final products.

However, it is apparent that the degradation of benzoyl peroxide and of retinoids is undesirable since it is detrimental to the effectiveness of the composition containing them.

Nothing would prompt the combination of these two active agents to obtain a stable composition, given that it was customarily known that the presence of benzoyl peroxide chemically and physically destabilized this type of composition.

Furthermore, those skilled in the art are constantly seeking to improve the efficacy and tolerance of compositions containing benzoyl peroxide and a naphthoic acid compound. One of the solutions for improving the efficacy is to increase the amounts of active agents present in the composition or to increase the treatment times. Such modifications generally result in an increase in the induced irritation. For this reason, it is necessary to provide compositions that can further improve the tolerance of the active ingredients.

SUMMARY OF THE INVENTION

The present invention provides compositions that are stable and less irritant than those of the prior art. Such compositions furthermore promote the topical penetration of the active ingredients in dispersed form.

Thus, it has now surprisingly, been demonstrated that ingredients that are known for providing a composition a film-forming effect may also improve the tolerance of the combination of two irritant active ingredients, such as anti-acne active ingredients, and in particular benzoyl peroxide and naphthoic acid compounds, such as adapalene.

Thus, the present invention provides compositions for topical application that are particularly effective, comprising at least one naphthoic acid compound and benzoyl peroxide, devoid of an obviously irritant effect that would prevent same from being used over a relatively long term by the individual.

This invention thus features compositions for topical application, comprising, in a physiologically acceptable medium, at least one naphthoic acid compound and benzoyl peroxide and at least one film-forming agent, said naphthoic acid compound being in a dispersed form in said composition.

Thus, the present invention features compositions, preferably pharmaceutical compositions, in particular for topical application, comprising, formulated into a physiologically acceptable medium, at least:
(i) one naphthoic acid compound,
(ii) benzoyl peroxide, and
(iii) a film-forming agent,
said naphthoic acid compound and said benzoyl peroxide being in a dispersed form in said composition.

According to the invention, the term "active agent in dispersed form" means an active ingredient in the form of solid particles, suspended in a given carrier. Such particles are in particular greater than 10 μm in size.

Advantageously, the particle size of the retinoid and of the benzoyl peroxide is such that at least 80% by number of the particles, and preferably at least 90% by number of the particles, have a diameter of less than 25 μm, and at least 99% by number of the particles have a diameter of less than 100 μm.

The present invention also features a process for formulating a composition for topical application, comprising the step of mixing a physiologically acceptable carrier including at least one naphthoic acid derivative and benzoyl peroxide with at least one film-forming agent, said naphthoic acid compound and the benzoyl peroxide being in a dispersed form in said composition. The term "physiologically acceptable carrier" means a carrier compatible with the skin, the mucous membranes and/or the integuments.

Finally, this invention also features the formulation of a composition as described above, into medicaments useful for the treatment and/or prevention of dermatological conditions/afflictions associated with a keratinization disorder relating to cell differentiation and proliferation, and in particular for preventing and/or treating comedonal acne, acne vulgaris, papulocomedonal acne, nodulocystic acne, polymorphic acne, acne rosacea, acne conglobata, senile acne, or else secondary acne such as solar acne, acne medicamentosa or occupational acne.

When a composition comprises, in a physiologically acceptable medium, at least one naphthoic acid compound, benzoyl peroxide and at least one film-forming agent, said naphthoic acid compound and the benzoyl peroxide being in a dispersed form in said composition, it shows very good tolerance without modifying the amount of active agent that has penetrated into the skin.

DETAILED DESCRIPTION OF BEST MODE AND SPECIFIC/PREFERRED EMBODIMENTS OF THE INVENTION

The compositions according to the invention comprise at least one naphthoic acid compound, benzoyl peroxide and at least one film-forming agent.

Naphthoic acid is a compound having the formula:

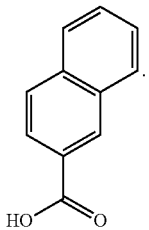

The term "naphthoic acid compound" means those compounds of formula (I):

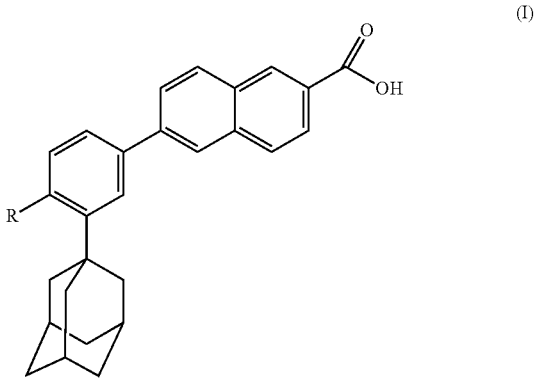

in which R is a hydrogen atom, a hydroxyl radical, a branched or unbranched alkyl radical having from 1 to 4 carbon atoms, an alkoxy radical having from 1 to 10 carbon atoms or a substituted or unsubstituted cycloaliphatic radical.

The term "linear or branched alkyl radical having from 1 to 4 carbon atoms" means, preferably, methyl, ethyl, propyl and butyl radicals.

The term "alkoxy radical having from 1 to 10 carbon atoms" means, preferably, methoxy, ethoxy, propoxy, butoxy, hexyloxy and decyloxy radicals.

The term "cycloaliphatic radical" means, preferably, monocyclic or polycyclic radicals such as the 1-methylcyclohexyl radical or the 1-adamantyl radical.

Among the naphthoic acid compounds that may be formulated into the compositions according to the invention, 6-[3-(1-adamantyl)-4-methoxyphenyl]-2-naphthoic acid (adapalene), 6-[3-(1-adamantyl)-4-hydroxyphenyl]-2-naphthoic acid, 6-[3-(1-adamantyl)-4-decyloxyphenyl]-2-naphthoic acid and 6-[3-(1-adamantyl)-4-hexyloxyphenyl]-2-naphthoic acid will advantageously be selected.

The abovementioned naphthoic acid compounds are generally in a dispersed form in the composition according to the invention. The insoluble naphthoic acid compounds are thus uniformly distributed in the compositions according to the invention.

In the compositions according to the invention, the naphthoic acid compounds are used at concentrations of less than or equal to 10% by weight relative to the total weight of the composition, and are preferably from 0.001% to 10% by weight relative to the total weight of the composition, and preferentially from 0.01% to 5%, more preferentially from 0.05% to 2%, and most preferentially from 0.1% to 0.3% by weight relative to the total weight of the composition.

Throughout the present text, unless otherwise specified, it is understood that, when concentration ranges are given, they include the upper and lower limits of said range.

Advantageously, the naphthoic acid compound in the compositions according to the invention is 6-[3-(1-adamantyl)-4-methoxyphenyl]-2-naphthoic acid (adapalene). Preferably, in the case of adapalene, the compositions according to the invention comprise from 0.001% to 5%, and advantageously from 0.01% to 1% by weight of adapalene, relative to the total weight of the composition, preferentially from 0.01% to 0.5%, preferably from 0.1% to 0.4% by weight of adapalene, more preferentially still at 0.1% or at 0.3% by weight of adapalene.

The subject compositions also comprise benzoyl peroxide (BPO).

In the compositions according to the invention, the benzoyl peroxide is included at concentrations ranging from 1% to 10% by weight, more particularly from 2% to 7% by weight, more preferentially still from 2.5% to 5% by weight, relative to the total weight of the composition.

The benzoyl peroxide may equally be in the free form or else in an encapsulated form in a form adsorbed onto, or absorbed into, any porous support.

It may, for example, be benzoyl peroxide encapsulated in a polymeric system composed of porous microspheres, for instance microsponges marketed under the trademark Microsponges P009A benzoyl peroxide by Cardinal Health.

The compositions according to the invention also comprise at least one film-forming agent.

The term "film-forming agent" means an ionic or nonionic hydrophilic polymer having a molecular mass at least greater than 10,000, which, during application to the skin, forms a continuous film. The applicant has demonstrated that these film-forming agents provide the compositions comprised thereof better tolerance.

Examples of film-forming agents, include the polyvinylpyrrolidones, which are preferably water-soluble, and soluble copolymers thereof, polysaccharides, with the exclusion of cellulose and derivatives thereof, in particular hydroxypropyl cellulose and xanthan gum, polyvinyl alcohols, acrylic copolymers and polyquaterniums.

Among the polyvinylpyrrolidones and derivatives thereof, exemplary are poly-1-vinyl-2-pyrrolidone, also known as povidone, or the polyvinylpyrrolidone/vinyl acetate copolymer, also known as copovidone, for instance Kollidon® VA64, Kollidon® 30, Kollidon® 90F or Kollidon® K17PF.

Examples of polysaccharides include the celluloses and derivatives, for instance carboxymethyl cellulose, and also exemplary are the pectins, gums such as karaya gum, and sodium hyaluronate marketed by Contipro.

Examples of polyvinyl alcohols are polyvinyl alcohols having a degree of polymerization from 500 to 5,000, a degree of hydrolysis from 85 to 89% to a viscosity from 20 to 65 mPa·s (4% (w/w) in water at 20° C.). More specifically, exemplary is Mowiol 40-88 marketed by Sigma Aldrich which has a degree of polymerization of 4200, a degree of hydrolysis from 86.7 to 88.7% to a viscosity from 38 to 42 mPa·s (4% (w/w) in water at 20° C.).

Among the acrylic copolymers, exemplary are the acrylates/dimethylaminoethyl methacrylate copolymer marketed under the trademark Eudragit E100 by Rohm & Haas, the acrylates/ammonium methacrylate copolymer marketed under the trademark Eudragit RS100 or Eudragit S100 by Rohm & Haas, the acrylates/octylacrylamide copolymer marketed under the trademark Dermacryl 79 by National Starch.

Among the polyquaterniums, exemplary are polyquaternium 1, 7 and 10, more particularly the polyquaternium-10 marketed under the trademark Celquat SC240C by National Starch.

Preferably, the film-forming agent is selected from among polyvinylpyrrolidones, which are preferably water-soluble, polysaccharides such as sodium hyaluronate, polyvinyl alcohols, acrylic copolymers and polyquaterniums.

Preferentially, the water-soluble film-forming agents according to the invention are selected from among polyvinylpyrrolidones, which are preferably water-soluble such as, for example Kollidon VA64, Kollidon 30 and Kollidon 90F marketed by BASF, from polysaccharides such as the sodium hyaluronate marketed under the trademark high molecular weight sodium hyaluronate by Contipro, from polyvinyl alcohols such as, for example, Mowiol 40-88 marketed by Sigma-Aldrich, from polyacrylamides such as, for example, Dermacryl 79 marketed by National Starch, from polyquaterniums such as, for example, polyquaternium 10 marketed under the trademark Celquat SC240C by National Starch.

In the compositions according to the invention, the film-forming agents are included at concentrations of less than or equal to 20%, preferably from 0.5% to 20% by weight, relative to the total weight of the composition, and more preferentially from 0.5% to 10%, and preferably from 0.5% to 6%, and in particular 0.5%, 1%, 2%, 3%, 4% or 6%.

The presence of at least one film-forming agent allows the tolerance to be improved and is particularly advantageous in the case of formulations comprising adapalene and benzoyl peroxide. The reason for this is that naphthoic acid derivatives may be irritant and may have a dehydrating action on the skin. It is therefore advantageous to reduce the irritation induced to be able to increase the doses.

The compositions of the present invention may be in any galenic form normally employed for topical application, in particular in the form of aqueous, aqueous-alcoholic or oily dispersions, suspensions, aqueous, anhydrous or lipophilic gels, emulsions (lotions, creams, ointments) of liquid, semi-solid or solid consistency obtained by dispersing a fatty phase in an aqueous phase (O/W) or vice versa (W/O) in the presence or absence of emulsifier, or else microemulsions, microcapsules, microparticles or vesicular dispersions of ionic and/or nonionic type.

Preferably, the compositions according to the invention are in the form of emulsions (lotions, creams or emulsifier-free creams), suspensions or gels, and more preferentially in the form of gels and emulsions.

Those skilled in the art will take care to select the excipients constituting the compositions according to the invention according to the desired galenic form and such that the advantageous properties of the composition according to the invention are respected.

The compositions of gel type according to the invention may also in particular comprise one or more of the following ingredients:
 a) one or more gelling agents and/or suspending agents and/or pH-independent gelling agents;
 b) optionally, one or more chelating agents;
 c) optionally, one or more emollients and/or humectants;
 d) one or more wetting agents;
 e) one or more additives.

The compositions of emulsion (cream, lotion, emulsifier-free cream) type according to the invention may also in particular comprise one or more of the following ingredients:
 a) one or more gelling agents and/or suspending agents and/or pH-independent gelling agents;
 b) optionally, one or more chelating agents;
 c) optionally, one or more emollients and/or humectants;
 d) one or more lipophilic excipients making up the fatty phase;
 e) optionally, one or more emulsifiers;
 f) one or more wetting agents;
 g) one or more additives.

Representative gelling agents and/or suspending agents and/or pH-independent gelling agents that may be included in the compositions according to the invention, exemplary are the acrylates/C10-30 alkyl acrylate crosspolymer marketed under the trademark Pemulen TR-1 or Pemulen TR-2 by Noveon, the "electrolyte-insensitive" carbomers marketed under the trademark Ultrez 20®, Ultrez 10®, Carbopol 1382®, Carbopol ETD2020NF®, Carbopol 980® or Carbopol 981® by Noveon, polysaccharides, non-limiting examples of which include xanthan gum such as Xantural 180® marketed by Kelco, gellan gum marketed under the trademark Kelcogel® by Kelco, guar gum, cellulose and derivatives thereof such as the microcrystalline cellulose and sodium carboxymethyl cellulose marketed under the trademark Avicel CL-611 by FMC Biopolymer, hydroxypropyl methyl cellulose, in particular the product marketed under the trademark Methocel E4M premium by Dow Chemical, or hydroxyethyl cellulose, in particular the product marketed under the trademark Natrosol HHX 250® by Aqualon, the family of magnesium aluminum silicates, such as the Veegum K marketed by Vanderbilt, the family of acrylic polymers coupled to hydrophobic chains, such as the PEG-150/decyl/SMDI copolymer marketed under the trademark Aculyn 44 (polycondensate comprising, as elements, at least one polyethylene glycol containing 150 or 180 mol of ethylene oxide, decyl alcohol and methylenebis(4-cyclohexylisocyanate) (SMDI), at 35% by weight in a mixture of propylene glycol (39%) and water (26%)), the family of modified starches such as the modified potato starch marketed under the trademark Structure Solanace, or else mixtures thereof, and the gelling agents of the polyacrylamide family, such as the sodium acryloyldimethyltaurate copolymer/isohexadecane/polysorbate 80 mixture marketed under the trademark Sepineo P 600® (or Simulgel 600 PHA®) by Seppic, the polyacrylamide/C13-14 isoparaffin/laureth-7 mixture, for instance that marketed under the trademark Sepigel 305 by Seppic, the family of carrageenans, in particular divided up into four main families: κ, λ, β, ω, such as Viscarin® and Gelcarin® marketed by IMCD.

The gelling agents as described above may be incorporated at the preferred concentrations ranging from 0.001% to 15%, and more preferentially ranging from 0.15% to 5%.

Preferred gelling agents, include the family of carbomers and in particular Carbopol Ultrez-20® and Carbopol ETD 2020®, the family of polyacrylamides and in particular the sodium acryloyldimethyltaurate copolymer/isohexadecane/polysorbate 80 mixture marketed under the trademark Sepineo P 600® (or Simulgel 600 PHA®), the family of polysaccharides and in particular the xanthan gum marketed under the trademark Xantural 180®, the family of celluloses and derivatives thereof and in particular the hydroxyethyl cellulose marketed under the trademark Natrosol 250HHX® and the hydroxypropyl methyl cellulose marketed under the trademark Methocel E4M Premium®, the family of acrylic polymers coupled to hydrophobic chains and in particular the PEG-150/decyl/SMDI copolymer marketed under the trademark Aculyn 44®.

Preferred gelling agents include carbomers, polyacrylamides, acrylic polymers coupled to hydrophobic chains, cellulose and derivatives thereof such as hydroxypropyl methyl cellulose or hydroxyethyl cellulose, polysaccharides and especially xanthan gum, and in particular those especially marketed under the trademarks Sepineo P 600® (or Simulgel 600 PHA®), PEG-150/decyl/SMDI copolymer, Methocel E4M Premium®, Natrosol HHX 250®, Xantural 180® and Carbopol Ultrez 20®.

Preferred suspending agents include microcrystalline cellulose and sodium carboxymethyl cellulose marketed under the trademark Avicel CL-611 by FMC Biopolymer.

Exemplary chelating agents, include ethylenediaminetetraacetic acid (EDTA), diethylenetriaminepentaacetic acid (DTPA), ethylenediaminebis(O-hydroxyphenylacetic acid) (EDDHA), hydroxyl-2-ethylenediaminetriacetic acid (HEDTA), ethyldiaminebis(O-hydroxy-p-methylphenyl) acetic acid (EDDHMA) and ethylenediaminebis(5-carboxy-2-hydroxyphenyl)acetic acid (EDDCHA).

A preferred chelating agent is ethylenediaminetetraacetic acid (EDTA) marketed in particular under the trademark Titriplex III®.

Among the humectants and/or emollients, the role of which is to hydrate the skin and to facilitate the application of the formulation, use is optionally made, without this list being limiting, of compounds such as glycerol and sorbitol, sugars (by way of example, glucose, lactose) polyethylene glycols (PEG) (by way of example, Lutrol E400), urea or amino acids (by way of example, serine, citrulline, arginine, asparagine, alanine).

A preferred humectant and/or emollient is glycerol.

Among the wetting agents, the role of which is to reduce the surface tension and to allow greater spreading of the liquid, use is preferentially made, without this list being limiting, of a wetting agent which may have preferentially an HLB of 10 to 14, compounds from the family of Poloxamers and/or glycols and more particularly Synperonic PE/L44 and/or Synperonic PE/L62 and/or compounds such as propylene glycol, dipropylene glycol, propylene glycol dipelargonate, lauroglycol, ethoxydiglycol. Preferably, the wetting agents are in liquid form so as to be easily incorporated into the composition without it being necessary to heat it.

A particularly preferred wetting agent is propylene glycol and Syperonic PE/L44 marketed by Uniqema.

The compositions according to the invention may comprise one or more emulsifiers.

Emulsifiers are amphiphilic compounds which contain a hydrophobic portion with affinity for oil and a hydrophilic portion with affinity for water, thus creating a link from the two phases. Ionic or nonionic emulsifiers thus stabilize oil/water emulsions by becoming adsorbed at the interface and by forming lamellar liquid crystal layers.

The emulsifying power of nonionic surfactants is closely linked to the polarity of the molecule. This polarity is defined by the HLB (hydrophilic/lipophilic balance).

A high HLB indicates that the hydrophilic fraction is predominant and, conversely, a low HLB indicates that the lipophilic portion is predominant. For example, HLB values of greater than approximately 10 correspond to hydrophilic surfactants.

Emulsifiers may be classified, according to their structure, under the generic terms "ionic" (anionic, cationic or amphoteric) or "nonionic". Nonionic emulsifiers are emulsifiers that do not dissociate into ions in water and are therefore insensitive to variations in pH.

Exemplary nonionic emulsifiers exhibiting a high HLB are sorbitan esters, such as POE(20) sorbitan monooleate, marketed under the trademark of Tween 80® (HLB=15), or POE (20) sorbitan monostearate, marketed under the trademark of Tween 60® (HLB=14.9), fatty alcohol ethers, such as POE (21) stearyl ether (HLB=15.5), marketed under the trademark Brij 721® by Uniqema, or ceteareth-20, marketed under the trademark Eumulgin B2® (HLB of 15.5) by Cognis, polyoxyethylene glycol esters, such as glyceryl stearate and PEG 100 stearate, marketed under the trademark Arlacel 165 FL® (HLB=11) by Uniqema, or PEG 6 stearate and PEG 32 stearate, marketed under the trademark Tefose 1500® (HLB=10) by Gatefossé, or sugar esters with a high HLB, such as PEG 20 methyl glucose sesquistearate, marketed under the trademark glucamate SSE20® (HLB=15) by Amerchol, and sucrose laurate, marketed under the trademark Surf hope C-1216® (HLB=16), and sucrose stearate, marketed under the trademark Surfhope C-1811® (HLB=11) and Surfhope SE Pharma D-1816® and sucrose palmitostearate marketed under the trademark Surf hope SE Pharma D-1616® by Gattefossé and polyglycerol esters. Preferably, said nonionic emulsifiers with a high HLB exhibit an HLB of from 10 and 18.

Exemplary nonionic emulsifiers exhibiting a low HLB (lipophilic emulsifiers) are sorbitan esters, such as sorbitan monostearate (HLB=4.7), marketed under the trademark Span 60 by Uniqema, glycerol esters, such as glycerol monostearate, marketed under the trademark Cutina GMS-VPH (HLB=3.8) by Cognis, polyethylene glycol esters, such as PEG-6 isostearate, marketed under the trademark Olepal Isostearique® (HLB=8) by Gattefossé, or sugar esters with a low HLB, such as methyl glucose sesquistearate, marketed under the trademark of Glucate SS® (HLB=6) by Amerchol, and sucrose dilaurate, marketed under the trademark of Surf hope C-1205® (HLB=5), and sucrose tristearate, marketed under the trademark of Surfhope C-1803® (HLB=3), by Gattefossé.

Also exemplary nonionic emulsifiers are self-emulsifying waxes that make it possible to obtain stable emulsions easily by simple dispersion at high temperature. By way of example, cetearyl alcohol (and) polysorbate 60 marketed under the trademark Polawax NF by Croda and Polawax GP200 marketed by Croda.

Preferably, one or more "high-HLB nonionic emulsifier"/"low-HLB nonionic emulsifier" pairs will be used as emulsifying system. It may in particular be a nonionic emulsifying system comprising at least one nonionic emulsifier with an HLB of greater than approximately 10 and at least one nonionic emulsifier with an HLB of less than approximately 10.

The ratio of each of the two surfactants forming the above-mentioned pair is most commonly determined by calculating the required HLB of the fatty phase used.

Preferred emulsifiers are:

hydrophilic emulsifiers of the type: glyceryl stearate and PEG-100 stearate marketed under the trademark Arlacel 165FL® by Uniqema, PEG 6 stearate and PEG 32 stearate marketed under the trademark Tefose 1500® by Gattefossé, PEG 20 methyl glucose sesquistearate marketed under the trademark Glucamate SSE20® by Amerchol, sucrose laurate marketed under the trademark Surfhope SE Pharma D-1216®, sucrose stearate marketed under the trademark Surfhope SE Pharma D-1816®, sucrose palmitostearate marketed under the trademark Surfhope SE Pharma D-1616®, Polyoxyethylene (21) stearyl ether marketed under the trademark Brij721® by Uniqema, Ceteareth-20 marketed under the trademark Eumulgin B2PH® by Cognis, and sorbitan esters marketed under the trademark Tween 80® and Tween 60®; and lipophilic emulsifiers of the type: methyl glucose sesquistearate such as Glucate SS® marketed by Amerchol, sucrose dilaurate such as Surfhope C-1205 and sucrose tristearate such as Surf hope C-1803.

The compositions according to the invention may also comprise a fatty phase. This fatty phase may comprise, for example, plant oils, mineral oils, animal oils, synthetic oils or silicone oils, and mixtures thereof.

Examples of mineral oils are liquid paraffins of various viscosities, such as Primol 352®, Marcol 82® and Marcol 152® marketed by Esso.

As plant oils, exemplary are sweet almond oil, palm oil, soybean oil, sesame oil, sunflower oil and olive oil.

As animal oils or their substitute of plant origin, exemplary are lanolin, squalene, fish oil with, as a derivative, the perhydrosqualene marketed under the trademark Sophiderm® by Sophim.

As synthetic oils, exemplary are an ester such as cetearyl isononanoate, for instance the product marketed under the trademark Cetiol SN PH® by Cognis France, diisopropyl adipate, for instance the product marketed under the trademark Crodamol DA® by Croda, isopropyl palmitate, for instance the product marketed under the trademark Crodamol IPP® by Croda, and caprylic/capric triglyceride, such as Miglyol 812® marketed by Univar.

As silicone oils, exemplary are dimethicone, for instance the product marketed under the trademark Q7-9120 Silicone Fluid® with a viscosity of 20 cst to 12,500 cst, by Dow Corning, or a cyclomethicone, for instance the product marketed under the trademark ST-Cyclomethicone 5NF®, also by Dow Corning.

As hydrogenated polyisobutene, exemplary is Parleam® marketed by Rossow.

As Guerbet alcohols, exemplary is octyldodecanol marketed under the trademark Eutanol G by Cognis.

For the compositions according to the invention, liquid paraffins and silicone oils and more particularly Marcol 152® and ST-Cyclomethicone 5NF®, are preferred.

It will also be possible to formulate solid fatty substances, such as natural or synthetic waxes, fatty acids, such as stearic acid, fatty alcohols, such as Speziol C18 Pharma, marketed by Cognis, and texturizing agents of tribehenate type, such as Compritol 888, marketed by Gattefossé, or hydrogenated castor oils, such as Cutina HR, marketed by Cognis. In this case, one skilled in the art will adjust the heating temperature of the preparation according to the presence or absence of these solids.

The compositions of the invention may also optionally comprise any additive normally employed in the cosmetic or pharmaceutical field, such as neutralizing agents of common inorganic or organic acid or base type (by way of example, triethanolamine, 10% sodium hydroxide solution, citric acid/sodium citrate buffer, succinic acid/sodium succinate buffer), sunscreens, antioxidants (butylhydroxyanisole type), fillers, electrolytes, preservatives, dyes, fragrances, essential oils, cosmetic active agents, moisturizers, vitamins, essential fatty acids, sphingolipids, self-tanning compounds such as DHA, calmatives and skin-protecting agents such as allantoin, or propenetrating agents, or a mixture thereof, and optionally a benzoyl peroxide-stabilizing agent (by way of example, sodium docusate or sodium C14-16 olefin sulfonate, lactic acid, citric acid) at a concentration of preferably from 0% to 2% relative to the total weight of the composition. Of course, those skilled in the art will take care to select this or these optional additional compound(s), and/or the amount thereof, in such a way that the advantageous properties of the composition according to the invention are not, or are not substantially, adversely affected.

These additives may be present in the composition in a proportion of from 0% to 20% by weight relative to the total weight of the composition.

Examples of preservatives include benzalkonium chloride, bronopol, chlorhexidine, chlorocresol and derivatives thereof, ethyl alcohol, phenoxyethanol, potassium sorbate, diazolidinylurea, benzyl alcohol, parabens or mixtures thereof.

Preferred preservatives include the parabens, phenoxyethanol or benzalkonium chloride, taken alone or as a mixture.

In one preferred embodiment, the composition is in gel form and comprises:
from 0.1% to 0.3% of a naphthoic acid compound;
from 1% to 10% of benzoyl peroxide;
from 30% to 95% of water;
from 0.5% to 10% of at least one film-forming agent;
from 0.10% to 3% of one or more gelling agents and/or suspending agents and/or pH-independent gelling agents;
from 0% to 1.5% of one or more chelating agents;
from 0.1% to 10% of one or more wetting agents;
from 0% to 20% of one or more humectants and/or emollients; and
from 0 to 20% of one or more additives.

In one particular embodiment of the invention, the composition is in the form of an oil-in-water (O/W) emulsion of lotion, cream or emulsifier-free cream type and comprises:
from 0.1% to 0.3% of a naphthoic acid compound;
from 1% to 10%, preferably from 2% to 5% of benzoyl peroxide;
from 30% to 95% of water;
from 0.5% to 10% of at least one film-forming agent;
from 0.1% to 3% of one or more gelling agents and/or suspending agents and/or pH-independent gelling agents;
from 0% to 1.5% of one or more chelating agents;
from 0.1% to 10% of one or more wetting agents;
from 0% to 20% of one or more humectants and/or emollients;
from 0 to 10% of emulsifiers;
from 0.1% to 30% of fatty phase; and
from 0% to 20% of one or more additives.

The present invention also features the compositions as described above, as medicaments. The compositions can in fact be formulated as a medicament.

This invention also features a process for formulating a composition as described above. Such a process is characterized in that it comprises the step of mixing a physiologically acceptable carrier comprising at least one naphthoic acid compound and benzoyl peroxide with at least one film-forming agent, to obtain a composition in which said naphthoic acid compound and benzoyl peroxide are in a dispersed form.

The other possible excipients and additives will be introduced according to the chemical nature of the compounds and the selected galenic form.

The introduction of the film-forming agent is dependent on the polymer. Thus, by way of example, Dermacryl 79 may be introduced into the fatty phase of emulsions and/or into the aqueous phase after the neutralization step. Also by way of example, sodium hyaluronate, Kollidon VA64, Kollidon 30, Kollidon 90F, Mowiol 40-88, and Celquat SC240C are introduced into the aqueous phase.

In particular, the present invention features a process for formulating a composition comprising the following steps:
a) preparation of active phase 1 comprising one of the two active agents;
b) preparation of active phase 2 comprising the other active agent;
c) preparation of the aqueous phase;
d) (optional) preparation of the film-forming phase;
e) mixing of the 2 active phases prepared in a) and b);
f) (optional) preparation of a fatty phase;
g) (optional) emulsification of the mixture of phases obtained in f) and c);
h) mixing of the phase obtained in g) or c) with the single active phase obtained in e);
i) (optional) addition of polyacrylamide;
j) (optional) neutralization of the formulation obtained in h);
k) (optional) addition of the film-forming phase;
l) (optional) adjustment with water.

The main process for formulating the composition according to the invention comprises, by way of example, the following steps:

Step a: Preparation of active phase 1:

Mixing purified water and active ingredient 1 (adapalene) with at least one wetting agent until said naphthoic acid compound is completely dispersed, to obtain active phase 1.

Step b: Preparation of Active Phase 2:

Mixing purified water and active ingredient 2 (benzoyl peroxide) with at least one wetting agent until said benzoyl peroxide is completely dispersed, to obtain active phase 2.

Step c: Preparation of the Aqueous Phase:

Introduced into a beaker, with stirring, if necessary at high temperature, are purified water and the gelling agent(s) and/or pH-independent gelling agent(s) (with the exclusion of polyacrylamide) and/or suspending agent(s) and optionally the chelating agent(s), the preservative(s), the hydrophilic emulsifier(s), the stabilizer(s), the humectant(s) and/or emollient(s), and the film-forming agent(s).

Step d: Optionally, Mixing at Least One Film-Forming Agent With Water to Obtain a Film-Forming Phase:

Step e: Mixing of the Active Phases:

The two active phases obtained respectively in a) and b) are mixed, and the stirring is maintained until complete homogenization.

Step f (Optionally for Obtaining an Emulsion): Preparation Of the Fatty Phase:

Mixing of the oily compounds, of the solid fatty substances and optionally of the lipophilic emulsifiers and the preservatives.

The mixture is heated and after homogenization the volatile silicone is introduced last, if present in the composition.

Step g (Optional): Emulsification:

At high temperature the fatty phase is introduced into the aqueous phase to carry out the emulsification. The heating is maintained for a few minutes, then the product is cooled.

Step h: Addition of the Single Active Phase:

The single active phase obtained in e) is introduced into the aqueous phase obtained in c) for gels or into the phase obtained in g) for emulsions.

Step i (Optional): Addition of Polyacrylamide:

Polyacrylamide is introduced, with stirring, into the phase obtained in h). The stirring is maintained until complete homogenization.

Step j: Neutralization:

The neutralizing agent for the gelling agent is introduced, if necessary, into the phase obtained in step h) or i).

Step k: (Optional) Addition of the Film-Forming Phase:

Addition of the film-forming phase prepared in step d) if the film-forming agent(s) have not been introduced into the aqueous phase.

Step l: (Optional) Adjustment with Water:

If necessary, an adjustment with water is carried out.

The alternative process for formulating the compositions according to the invention comprises, by way of example, the following steps:

The active ingredients are mixed in the $1^{st}$ step of the process described above; thus, steps a) and b) are replaced with step a'):

a') preparation of the single active phase comprising the two active agents.

The process is then continued as described starting from step c) with elimination of step e).

In more detail, the main process for preparing the composition according to the invention comprises the following steps:

Step a: Preparation of Active Phase 1:

Introduced into a beaker, with stirring, are purified water, the active ingredient (adapalene) and the wetting agents (of the type Synperonic PE/L62, Synperonic PE/L44, propylene glycol). The mixture is stirred until complete dispersion.

Step b: Preparation of Active Phase 2:

Introduced into a beaker, with stirring, are purified water, the active ingredient (benzoyl peroxide) and the wetting agents (of the type Synperonic PE/L62, Synperonic PE/L44, propylene glycol). The mixture is stirred until complete dispersion.

Step c: Preparation of the Aqueous Phase:

Introduced into a beaker, with stirring, if necessary at high temperature, are purified water and the gelling agent(s) (of the type Carbopol Ultrez 20, ETD2020 NF, Xantural 180, Natrosol 250 HHX) and/or pH-independent gelling agent(s) (with the exclusion of Simulgel 600 PHA) and/or suspending agent(s) (of Avicel CL611 type) and optionally the chelating agent(s) (of EDTA type), the preservative(s) (of methyl paraben type), the stabilizer(s) (of sodium docusate type), the emollient(s) and/or humectant(s) (of glycerol type), and the film-forming agent(s) (of sodium hyaluronate type).

Step d: Optionally, Mixing at Least One Film-Forming Agent (of Kollidon, Etc. Type) with Water to Obtain a Film-Forming Phase:

Step e: Mixing of the Active Phases:

The two active phases obtained respectively in a) and b) are mixed, and the stirring is maintained until complete homogenization.

Step f (Optional): Preparation of the Fatty Phase:

Mixing of the oils and solid fatty substances (of the type Olepal Isostearique, Cetiol SN PH, Crodamol DA, Speziol C18, Cosbiol) and optionally of the emulsifiers (of the type Glucate SS, Glucamate SSE 20, Brij 721, Tefose 1500) and the preservatives (of phenoxyethanol and propyl paraben type).

The mixture is heated and after homogenization the volatile silicone (of Cyclomethicone 5NF type) is introduced last, if present in the composition.

Step g (Optional): Emulsification:

At high temperature the fatty phase is introduced into the aqueous phase to carry out the emulsification. The heating is maintained for a few minutes, then stopped to cool the product.

Step h: Addition of the Single Active Phase:

The single active phase obtained in e) is introduced into the aqueous phase obtained in c) for gels or into the phase obtained in g) for emulsions.

Step i (Optional): Addition of Simulgel 600PHA:

Simulgel 600PHA is introduced, with stirring, into the phase obtained in h). The stirring is maintained until complete homogenization.

Step j: Neutralization:

If necessary, the neutralizing agent for the gelling agent (of the type triethanolamine or 10% sodium hydroxide solution) is introduced into the phase obtained in step h) or i).

Step k: (Optional) Addition of the Film-Forming Phase:

Addition of the film-forming phase prepared in step d) if the film-forming agent(s) have not been introduced into the aqueous phase.

Step l: (Optional) Adjustment with Water:

If necessary, an adjustment with water is carried out.

In more detail, the alternative process for preparing the composition according to the invention comprises the following steps:

The active ingredients are mixed in the $1^{st}$ step of the process described above; thus, steps a) and b) are replaced with step a'):

a') Preparation of the single active phase comprising the two active agents.

The naphthoic acid compound and the benzoyl peroxide are mixed with at least one wetting agent, in water, until said benzoyl peroxide and said naphthoic acid derivative are completely dispersed, to obtain a single active phase, according to the same operating conditions.

The process is then continued as described starting from step c) and step e) is eliminated.

The present invention also features the use of the novel composition as described above, in cosmetics and in dermatology.

In particular, the present invention features formulation of a composition as described above into pharmaceutical compositions useful for the treatment and/or prevention of dermatological conditions or afflictions associated with a keratinization disorder relating to cell differentiation and proliferation, in particular for treating acne vulgaris, comedonal acne, papulopustular acne, papulocomedonal acne, nodulocystic acne, acne conglobata, acne keloid of the nape of the neck, recurrent miliary acne, acne necrotica, acne neonatorum, occupational acne, senile acne, solar acne and acne medicamentosa. More particularly, this features the treatment and/or prevention of dermatological conditions, afflictions or disorders associated with a keratinization disorder related to cell differentiation and proliferation, in particular for treating, whether regime or regimen, acne vulgaris, comedonal acne, papulopustular acne, papulocomedonal acne, nodulocystic acne, acne conglobata, acne keloid of the nape of the neck, recurrent miliary acne, acne necrotica, acne neonatorum, occupational acne, acne rosacea, senile acne, solar acne and acne medicamentosa.

More particularly, the present invention features formulation of a composition as described above, into pharmaceutical compositions useful for preventing and/or treating acne vulgaris.

Preferentially, said compositions according to the invention are administered topically. The term "topically" means administration to the skin, the integuments or the mucous membranes.

In addition, the present invention also features the cosmetic application of the subject compositions for the treatment of acne-prone skin, for combating the greasy appearance of the skin or the hair, in protection against the harmful effects of sunlight, or in the treatment of physiologically greasy skin, or for preventing and/or combating photo-induced or chronological aging.

The present invention will now be illustrated by means of the physical and chemical stability data presented below.

The physical stability of the formulations is monitored by macroscopic and microscopic observation of the formulation stored at room temperature at T0, T+1 month, T+2 months and T+3 months.

At RT, macroscopic observation makes it possible to guarantee the physical integrity of the products.

Microscopic observation makes it possible to evaluate the quality of the dispersion of the two active agents. Adapalene is observed in fluorescent light while benzoyl peroxide is observed in polarized light.

The characterization of the final product is completed by a yield point measurement and a viscosity measurement.

A Haake rheometer of VT550 type with an SVDIN measuring spindle is used for measuring the yield point.

The rheograms are produced at 25° C. and at a rate set from 0 to 100 $s^{-1}$. The viscosity values are recorded at constant shear values of 4 $s^{-1}$, 20 $s^{-1}$ and 100 $s^{-1}$ ($\gamma$). The term "yield point" ($\tau_0$ expressed in pascals) means the force necessary (minimum shear stress) to overcome the cohesive forces of van der Waals type and to bring about flow.

Viscometers of Brookfield RVDVII+ and LDVDII+ type are used for the viscosity measurements.

The viscosity ranges which can be measured with these two types of Brookfield viscometers are the following:

RVDVII+ viscometer: 100 cP-40 McP
LVDVII+ viscometer: 15 cP-6 McP

For the emulsions, it is considered that there is present, at the starting time T0:
a cream if the viscosity is greater than 30,000 cP
a lotion if the viscosity is less than 30,000 cP (Lucinda Buhse, ACPS Oct. 22, 2003, Pharmaceutical nomenclature—Issues and challenges).

The chemical stability is ensured by an HPLC assay of adapalene and by an iodometric assay for benzoyl peroxide.

The results are expressed in g/g of adapalene and of benzoyl peroxide and as % with respect to the theoretical titre.

To further illustrate the present invention and the advantages thereof, the following specific examples are given, it being understood that same are intended only as illustrative and in nowise limitative. In said examples to follow, all parts and percentages are given by weight, unless otherwise indicated.

EXAMPLES

Example 1

Formulation of Gel Type Containing 5% Benzoyl Peroxide, 0.1% Adapalene and 4% Kollidon VA64 (Copovidone) as Film-Forming Agent The composition is formulated according to the procedure described by the main and/or alternative process.

Constituents Content (% w/w):

| | |
|---|---|
| Benzoyl peroxide | 5.00 |
| Adapalene | 0.10 |
| Propylene glycol | 4.00 |
| Synperonic PE/L44 | 0.20 |
| EDTA | 0.10 |
| Glycerol | 4.00 |
| Kollidon VA64 | 4.00 |
| Sodium docusate | 0.05 |
| Simulgel 600PHA | 4.00 |
| Purified water | qs 100% |

Stability Data:
Physical Stability:

| Characterization at T0 | |
|---|---|
| Macroscopic appearance | White gel |
| Microscopic appearance | Dispersion of the active agents without aggregates >100 μm |
| pH | 4.47 |
| Viscosity data  Haake (4 $s^{-1}$/20 $s^{-1}$/100 $s^{-1}$) | 143/208/356 |
| Brookfield RVDVII+ (S29; 5 rpm) | 95 400 cP |

| | T + 1 month | T + 2 months | T + 3 months |
|---|---|---|---|
| Macroscopic appearance RT | Identical to T0 | Identical to T0 | Identical to T0 |
| Microscopic appearance RT | Identical to T0 | Identical to T0 | Identical to T0 |
| pH RT | 4.14 | 4.07 | 4.02 |
| Haake rheology (4 $s^{-1}$/20 $s^{-1}$/100 $s^{-1}$) | 130/178/321 | 130/184/327 | 115/174/339 |
| Brookfield RVDVII+ (S29; 5 rpm) | 89 600 cP | 98 000 cP | 101 000 cP |

Chemical Stability:
Adapalene:

| | | Time | | | |
|---|---|---|---|---|---|
| Stability conditions | | T0 | T + 1 month | T + 2 months | T + 3 months |
| RT | g/g | 0.106 | 0.103 | 0.111 | 0.099 |
| | % of theoretical titre | 106 | 103 | 111 | 99 |

Benzoyl Peroxide:

| Stability conditions | | T0 | T + 1 month | T + 2 months | T + 3 months |
|---|---|---|---|---|---|
| | | | Time | | |
| RT | g/g | 5.40 | 4.97 | 5.46 | 4.89 |
| | % of theoretical titre | 108 | 99 | 109 | 98 |

Example 2

Formulation of Gel Type Containing 2.5% Benzoyl Peroxide, 0.1% Adapalene and 2% Sodium Hyaluronate as Film-Forming Agent The composition is formulated according to the procedure described by the main and/or alternative process.

Constituents Content (% w/w):

| | |
|---|---|
| Benzoyl peroxide | 2.50 |
| Adapalene | 0.10 |
| Propylene glycol | 4.00 |
| Synperonic PE/L44 | 0.20 |
| EDTA | 0.10 |
| Glycerol | 4.00 |
| Sodium hyaluronate | 2.00 |
| Simulgel 600PHA | 2.00 |
| Purified water | qs 100% |

Stability Data:
Physical Stability:

| Characterization at T0 | | |
|---|---|---|
| Macroscopic appearance | | White gel |
| Microscopic appearance | | Dispersion of the active agents without aggregates >100 μm |
| pH | | 5.15 |
| Viscosity data | Haake (4 s⁻¹/20 s⁻¹/100 s⁻¹) | 241/433/564 |
| | Brookfield RVDVII+ (S29; 5 rpm) | 135 000 cP |

| | | T + 1 month | T + 2 months | T + 3 months |
|---|---|---|---|---|
| Macroscopic appearance | RT | Identical to T0 | Identical to T0 | Identical to T0 |
| Microscopic appearance | RT | Identical to T0 | Identical to T0 | Identical to T0 |
| pH | RT | 4.99 | 4.64 | 4.87 |
| Haake rheology (4 s⁻¹/20 s⁻¹/100 s⁻¹) | | 221/412/625 | 244/446/647 | 266/456/677 |
| Brookfield RVDVII+ (S29; 5 rpm) | | 135 000 cP | 127 000 cP | 129 000 cP |

Chemical Stability:
Adapalene:

| Stability conditions | | T0 | T + 1 month | T + 2 months | T + 3 months |
|---|---|---|---|---|---|
| | | | Time | | |
| RT | g/g | 0.090 | 0.096 | 0.100 | 0.101 |
| | % of theoretical titre | 90 | 96 | 100 | 101 |

Benzoyl Peroxide:

| Stability conditions | | T0 | T + 1 month | T + 2 months | T + 3 months |
|---|---|---|---|---|---|
| | | | Time | | |
| RT | g/g | 2.53 | 2.51 | 2.60 | 2.52 |
| | % of theoretical titre | 101 | 100 | 104 | 101 |

Example 3

Formulation of Gel Type Containing 0.1% Adapalene, 2.5% Benzoyl Peroxide, and 4% Kollidon 30 as Film-Forming Agent The composition is formulated according to the procedure described by the main and/or alternative process.

Constituents Content (% w/w):

| | |
|---|---|
| Benzoyl peroxide | 2.50 |
| Adapalene | 0.10 |
| Propylene glycol | 4.00 |
| Synperonic PE/L44 | 0.20 |
| EDTA | 0.10 |
| Glycerol | 4.00 |
| Sodium docusate | 0.05 |
| Kollidon 30 | 4.00 |
| Simulgel 600PHA | 4.00 |
| Purified water | qs 100% |

Stability Data:
Physical Stability:

| Characterization at T0 | | |
|---|---|---|
| Macroscopic appearance | | White gel |
| Microscopic appearance | | Dispersion of the active agents without aggregates >100 μm |
| pH | | 3.96 |
| Viscosity data | Haake (4 s⁻¹/20 s⁻¹/100 s⁻¹) | 148/204/345 |
| | Brookfield RVDVII+ (S29; 5 rpm) | 106 000 cP |

| | | T + 1 month |
|---|---|---|
| Macroscopic appearance | RT | Identical to T0 |
| Microscopic | RT | Identical |

-continued

|  |  | T + 1 month |
|---|---|---|
| appearance | RT | to T0 |
| pH |  | 3.93 |
| Haake rheology<br>(4 s$^{-1}$/20 s$^{-1}$/100 s$^{-1}$) |  | 160/226/368 |
| Brookfield RVDVII+<br>(S29; 5 rpm) |  | 115 000 cP |

Chemical Stability:
Adapalene:

|  |  | Time | |
|---|---|---|---|
| Stability<br>conditions |  | T0 | T + 1<br>month |
| RT | g/g | 0.096 | 0.096 |
|  | % of<br>theoretical<br>titre | 96 | 96 |

Benzoyl Peroxide:

|  |  | Time | |
|---|---|---|---|
| Stability<br>conditions |  | T0 | T + 1<br>month |
| RT | g/g | 2.457 | 2.440 |
|  | % of<br>theoretical<br>titre | 98 | 98 |

Example 4

Formulation of Gel Type Containing 0.1%
Adapalene, 2.5% Benzoyl Peroxide, and 2%
Polyvinyl Alcohol as Film-Forming Agent The composition is formulated according to the procedure described by the main and/or alternative process.
Constituents Content (% m/m):

| Benzoyl peroxide | 2.50 |
|---|---|
| Adapalene | 0.10 |
| Propylene glycol | 4.00 |
| Synperonic PE/L44 | 0.20 |
| EDTA | 0.10 |
| Glycerol | 4.00 |
| Sodium docusate | 0.05 |
| Mowiol 40-88 | 2.00 |
| Simulgel 600PHA | 4.00 |
| Purified water | qs 100% |

Stability Data:
Physical Stability:

| Characterization at T0 | |
|---|---|
| Macroscopic appearance | White gel |
| Microscopic appearance | Dispersion of the active agents without aggregates >100 μm |
| pH | 4.91 |

-continued

| Characterization at T0 | | |
|---|---|---|
| Viscosity<br>data | Haake<br>(4 s$^{-1}$/20 s$^{-1}$/100 s$^{-1}$) | 169/254/487 |
|  | Brookfield RVDVII+<br>(S29; 5 rpm) | 117 000 cP |

|  |  | T + 1 month |
|---|---|---|
| Macroscopic<br>appearance | RT | Identical<br>to T0 |
| Microscopic<br>appearance | RT | Identical<br>to T0 |
| pH | RT | 4.37 |
| Haake rheology<br>(4 s$^{-1}$/20 s$^{-1}$/100 s$^{-1}$) |  | 186/313/611 |
| Brookfield RVDVII+<br>(S29; 5 rpm) |  | 114 000 cP |

Chemical Stability:
Adapalene:

|  |  | Time | |
|---|---|---|---|
| Stability<br>conditions |  | T0 | T + 1<br>month |
| RT | g/g | 0.098 | 0.097 |
|  | % of<br>theoretical<br>titre | 98 | 97 |

Benzoyl Peroxide:

|  |  | Time | |
|---|---|---|---|
| Stability<br>conditions |  | T0 | T + 1<br>month |
| RT | g/g | 2.515 | 2.450 |
|  | % of<br>theoretical<br>titre | 100.6 | 98 |

Example 5

Formulation of Gel Type Containing 0.1%
Adapalene, 2.5% Benzoyl Peroxide, and 1% Celquat
SC240C as Film-Forming Agent The composition is formulated according to the procedure described by the main and/or alternative process.
Constituents Content (% w/w):

| Benzoyl peroxide | 2.50 |
|---|---|
| Adapalene | 0.10 |
| Propylene glycol | 4.00 |
| Synperonic PE/L44 | 0.20 |
| EDTA | 0.10 |
| Glycerol | 4.00 |
| Sodium docusate | 0.05 |
| Celquat SC240C | 1.00 |
| Natrosol 250HHX | 0.80 |
| Purified water | qs 100% |

Example 6

Formulation of Cream Type Containing 0.1% Adapalene, 2.5% Benzoyl Peroxide, and 0.5% Sodium Hyaluronate as Film-Forming Agent The composition is formulated according to the procedure described by the main and/or alternative process.

Constituents Content (% w/w):

| | |
|---|---|
| Benzoyl peroxide | 2.50 |
| Adapalene | 0.10 |
| Propylene glycol | 5.00 |
| Synperonic PE/L44 | 0.20 |
| EDTA | 0.10 |
| Glycerol | 5.00 |
| Carbopol Ultrez 20 | 0.70 |
| Marcol 152 | 7.00 |
| Sodium hyaluronate | 0.50 |
| BHA | 0.005 |
| Purified water | qs 100% |

Example 7

Formulation of Cream Type Containing 0.1% Adapalene, 2.5% Benzoyl Peroxide, and 6% Kollidon VA64 (Copovidone) as Film-Forming Agent The composition is formulated according to the procedure described by the main and/or alternative process.

Constituents Content (% w/w):

| | |
|---|---|
| Benzoyl peroxide | 2.50 |
| Adapalene | 0.10 |
| Propylene glycol | 6.00 |
| Synperonic PE/L44 | 0.20 |
| Sodium docusate | 0.05 |
| EDTA | 0.10 |
| Carbopol Ultrez 20 | 0.20 |
| Glycerol | 3.00 |
| Glucamate SSE 20 | 3.50 |
| Glucate SS | 3.50 |
| Perhydrosqualene | 6.00 |
| ST-Cyclomethicone 5NF | 13.00 |
| Kollidon VA64 | 6.00 |
| Purified water | qs 100% |
| Triethanolamine | qs pH 5.5 ± 0.5 |

Stability Data:

Physical Stability:

| Characterization at T0 | |
|---|---|
| Macroscopic appearance | White cream |
| Microscopic appearance | Dispersion of the active agents without aggregates >100 μm |
| pH | 5.28 |
| Viscosity data | Haake ($4 s^{-1}/20 s^{-1}/100 s^{-1}$) 78/104/173 |
| | Brookfield RVDVII+ (S31; 5 rpm) 42 560 cP |

| | T + 1 month | T + 2 months | T + 3 months |
|---|---|---|---|
| Macroscopic appearance RT | Identical to T0 | Identical to T0 | Identical to T0 |
| Microscopic appearance RT | Identical to T0 | Identical to T0 | Identical to T0 |
| pH RT | 4.95 | 4.89 | 4.98 |
| Haake rheology ($4 s^{-1}/20 s^{-1}/100 s^{-1}$) | 64/94/158 | 65/91/155 | 58/84/140 |
| Brookfield RVDVII+ (S31; 5 rpm) | 41 216 cP | 36 544 cP | 32 832 cP |

Chemical Stability:

Adapalene:

| | | Time | | | |
|---|---|---|---|---|---|
| Stability conditions | | T0 | T + 1 month | T + 2 months | T + 3 months |
| RT | g/g | 0.097 | 0.126 | 0.107 | 0.096 |
| | % of theoretical titre | 97 | 126 | 107 | 96 |

Benzoyl Peroxide:

| | | Time | | | |
|---|---|---|---|---|---|
| Stability conditions | | T0 | T + 1 month | T + 2 months | T + 3 months |
| RT | g/g | 2.45 | 2.90 | 2.78 | 2.38 |
| | % of theoretical titre | 98 | 116 | 112 | 95 |

Example 8

Formulation of Cream Type Containing 0.3% Adapalene, 5% Benzoyl Peroxide, and 1% Sodium Hyaluronate as Film-Forming Agent The composition is formulated according to the procedure described by the main and/or alternative process.

Constituents Content (% w/w):

| | |
|---|---|
| Benzoyl peroxide | 5.00 |
| Adapalene | 0.30 |
| Dipropylene glycol | 5.00 |
| Synperonic PE/L44 | 0.20 |
| Glycerol | 7.00 |
| EDTA | 0.10 |
| Eumulgin B2 PH | 3.00 |
| Arlacel 165FL | 3.00 |
| Speziol C18 Pharma | 2.00 |
| Mygliol 812 N | 7.00 |
| ST-Cyclomethicone 5NF | 6.00 |
| Simulgel 600PHA | 2.00 |
| Sodium hyaluronate | 1.00 |
| Purified water | qs 100% |

Stability Data:
Physical Stability:

| Characterization at T0 | | |
|---|---|---|
| Macroscopic appearance | | White cream |
| Microscopic appearance | | Dispersion of the active agents without aggregates >100 μm |
| pH | | 5.25 |
| Viscosity data | Haake (4 s$^{-1}$/20 s$^{-1}$/100 s$^{-1}$) | 162/265/364 |
| | Brookfield RVDVII+ (S34; 5 rpm) | 89 600 cP |

| | | T + 1 month | T + 2 months | T + 3 months |
|---|---|---|---|---|
| Macroscopic appearance | RT | Identical to T0 | Identical to T0 | Identical to T0 |
| Microscopic appearance | RT | Identical to T0 | Identical to T0 | Identical to T0 |
| pH | RT | 4.85 | 4.75 | 4.79 |
| Haake rheology (4 s$^{-1}$/20 s$^{-1}$/100 s$^{-1}$) | | 141/226/340 | 146/239/348 | 140/229/335 |
| Brookfield RVDVII+ (S34; 5 rpm) | | 92 240 cP | 90 880 cP | 91 136 cP |

Chemical Stability:
Adapalene:

| | | Time | | | |
|---|---|---|---|---|---|
| Stability conditions | | T0 | T + 1 month | T + 2 months | T + 3 months |
| RT | g/g | 0.289 | 0.284 | 0.290 | 0.295 |
| | % of theoretical titre | 96 | 95 | 97 | 97 |

Benzoyl Peroxide:

| | | Time | | | |
|---|---|---|---|---|---|
| Stability conditions | | T0 | T + 1 month | T + 2 months | T + 3 months |
| RT | g/g | 4.99 | 4.87 | 4.89 | 4.88 |
| | % of theoretical titre | 100 | 97.4 | 98 | 98 |

Example 9

Formulation of Cream Type Containing 0.1% Adapalene, 5% Benzoyl Peroxide, and 4% Kollidon VA64 (Copovidone) As Film-Forming Agent The composition is formulated according to the procedure described by the main and/or alternative process.
Constituents Content (% w/w):

| Benzoyl peroxide | 5.00 |
|---|---|
| Adapalene | 0.10 |
| Propylene glycol | 6.00 |
| Synperonic PE/L44 | 0.20 |
| EDTA | 0.10 |
| Glycerol | 7.00 |
| Natrosol 250HHX | 0.20 |
| Eumulgin B2 PH | 3.00 |
| Speziol C18 pharma | 2.00 |
| Miglyol 812 N | 7.00 |
| Arlacel 165 FL | 3.00 |
| ST-Cyclomethicone 5NF | 6.00 |
| Simulgel 600PHA | 2.00 |
| Kollidon VA64 | 4.00 |
| Purified water | qs 100% |
| Triethanolamine | qs pH 5.5 ± 0.5 |

Stability Data:
Physical Stability:

| Characterization at T0 | | |
|---|---|---|
| Macroscopic appearance | | |
| Microscopic appearance | | Dispersion of the active agents without aggregates >100 μm |
| pH | | 5.31 |
| Viscosity data | Haake (4 s$^{-1}$/20 s$^{-1}$/100 s$^{-1}$) | 203/266/378 |
| | Brookfield RVDVII+ (S29; 5 rpm) | 183 000 cP |

| | | T + 1 month | T + 2 months | T + 3 months |
|---|---|---|---|---|
| Macroscopic appearance | RT | Identical to T0 | Identical to T0 | Identical to T0 |
| Microscopic appearance | RT | Identical to T0 | Identical to T0 | Identical to T0 |
| pH | RT | 4.77 | 4.59 | 4.61 |
| Haake rheology (4 s$^{-1}$/20 s$^{-1}$/100 s$^{-1}$) | | 227/274/402 | 219/258/395 | 218/274/413 |
| Brookfield RVDVII+ (S29; 5 rpm) | | 149 000 cP | 178 000 cP | 175 000 cP |

Chemical Stability:
Adapalene:

| | | Time | | | |
|---|---|---|---|---|---|
| Stability conditions | | T0 | T + 1 month | T + 2 months | T + 3 months |
| RT | g/g | 0.093 | 0.092 | 0.093 | 0.093 |
| | % of theoretical titre | 93 | 92 | 93 | 93 |

Benzoyl Peroxide:

| | | Time | | | |
|---|---|---|---|---|---|
| Stability conditions | | T0 | T + 1 month | T + 2 months | T + 3 months |
| RT | g/g | 4.89 | 4.67 | 4.78 | 4.72 |
| | % of theoretical titre | 98 | 93 | 96 | 94 |

Example 10

Formulation of Fluid Cream Type Containing 0.1% Adapalene, 2.5% Benzoyl Peroxide, and 0.5% Sodium Hyaluronate as Film-Forming Agent The Composition is Formulated According to the Procedure described by the main and/or alternative process.

Constituents Content (% w/w):

| | |
|---|---|
| Benzoyl peroxide | 2.50 |
| Adapalene | 0.10 |
| Propylene glycol | 5.00 |
| Synperonic PE/L44 | 0.20 |
| EDTA | 0.10 |
| Glycerol | 5.00 |
| Carbopol Ultrez 20 | 0.70 |
| Marcol 152 | 7.00 |
| Sodium hyaluronate | 0.50 |
| Purified water | qs 100% |
| 10% sodium hydroxide | qs pH 5.5 +/− 0.5 |

Stability Data:

Physical Stability:

| Characterization at T0 | |
|---|---|
| Macroscopic appearance | White cream |
| Microscopic appearance | Dispersion of the active agents without aggregates >100 μm |
| pH | 5.14 |
| Viscosity data | Haake ($4\ s^{-1}/20\ s^{-1}/100\ s^{-1}$) 76/126/167 |
| | Brookfield RVDVII+ (S31; 5 rpm) 39 040 cP |

| | | T + 1 month | T + 2 months | T + 3 months |
|---|---|---|---|---|
| Macroscopic appearance | RT | Identical to T0 | Identical to T0 | Identical to T0 |
| Microscopic appearance | RT | Identical to T0 | Identical to T0 | Identical to T0 |
| pH | RT | 4.98 | 4.97 | 5.16 |
| Haake rheology ($4\ s^{-1}/20\ s^{-1}/100\ s^{-1}$) | | 68/123/187 | 74/126/189 | 64/117/179 |
| Brookfield RVDVII+ (S31; 5 rpm) | | 34 816 cP | 33 408 cP | 35 328 cP |

Chemical Stability:

Adapalene:

| | | Time | | | |
|---|---|---|---|---|---|
| Stability conditions | | T0 | T + 1 month | T + 2 months | T + 3 months |
| RT | g/g | 0.098 | 0.10 | 0.099 | 0.099 |
| | % of theoretical titre | 98 | 100 | 99 | 99 |

Benzoyl Peroxide:

| | | Time | | | |
|---|---|---|---|---|---|
| Stability conditions | | T0 | T + 1 month | T + 2 months | T + 3 months |
| RT | g/g | 2.62 | 2.53 | 2.61 | 2.57 |
| | % of theoretical titre | 105 | 101 | 104 | 103 |

Example 11

Formulation of Cream Type Containing 0.1% Adapalene, 2.5% Benzoyl Peroxide, and 4% Kollidon VA64 (Copovidone) as Film-Forming Agent The composition is formulated according to the procedure described by the main and/or alternative process.

Constituents Content (% w/w):

| | |
|---|---|
| Benzoyl peroxide | 2.50 |
| Adapalene | 0.10 |
| Propylene glycol | 5.00 |
| Synperonic PE/L44 | 0.20 |
| Glycerol | 5.00 |
| ST-Cyclomethicone 5NF | 7.00 |
| Kollidon VA64 | 4.00 |
| Simulgel 600PHA | 3.00 |
| Purified water | qs 100% |

Stability Data:

Physical stability:

| Characterization at T0 | |
|---|---|
| Macroscopic appearance | White cream |
| Microscopic appearance | Dispersion of the active agents without aggregates >100 μm |
| pH | 4.52 |
| Viscosity data | Haake ($4\ s^{-1}/20\ s^{-1}/100\ s^{-1}$) 197/267/400 |
| | Brookfield RVDVII+ (S29; 5 rpm) 145 000 cP |

| | | T + 1 month | T + 2 months | T + 3 months |
|---|---|---|---|---|
| Macroscopic appearance | RT | Identical to T0 | Identical to T0 | Identical to T0 |
| Microscopic appearance | RT | Identical to T0 | Identical to T0 | Identical to T0 |
| pH | RT | 4.00 | 3.87 | 3.81 |
| Haake rheology ($4\ s^{-1}/20\ s^{-1}/100\ s^{-1}$) | | 182/248/420 | 180/251/403 | 171/243/405 |
| Brookfield RVDVII+ (S29; 5 rpm) | | 138 000 cP | 131 000 cP | 124 000 cP |

Chemical Stability:

Adapalene:

| Stability conditions | | Time | | | |
|---|---|---|---|---|---|
| | | T0 | T + 1 month | T + 2 months | T + 3 months |
| RT | g/g | 0.098 | 0.098 | 0.096 | 0.099 |
| | % of theoretical titre | 98 | 98 | 96 | 99 |

Benzoyl Peroxide:

| Stability conditions | | Time | | | |
|---|---|---|---|---|---|
| | | T0 | T + 1 month | T + 2 months | T + 3 months |
| RT | g/g | 2.57 | 2.46 | 2.51 | 2.48 |
| | % of theoretical titre | 103 | 98 | 100 | 99 |

Example 12

Formulation of Cream Type Containing 0.1% Adapalene, 2.5% Benzoyl Peroxide, and 4% Kollidon 90F as Film-Forming Agent The composition is formulated according to the procedure described by the main and/or alternative process.

Constituents Content (% w/w):

| Benzoyl peroxide | 2.50 |
|---|---|
| Adapalene | 0.10 |
| Propylene glycol | 6.00 |
| Synperonic PE/L44 | 0.20 |
| Sodium docusate | 0.05 |
| EDTA | 0.10 |
| Carbopol Ultrez 20 | 0.20 |
| Glycerol | 3.00 |
| Glucamate SSE 20 | 3.50 |
| Glucate SS | 3.50 |
| Sophiderm | 6.00 |
| ST-Cyclomethicone 5NF | 13.00 |
| Kollidon 90F | 4.00 |
| Purified water | qs 100% |
| Triethanolamine | qs pH 5.5 ± 0.5 |

Stability Data:

Physical stability:

| Characterization at T0 | | |
|---|---|---|
| Macroscopic appearance | | White cream |
| Microscopic appearance | | Dispersion of the active agents without aggregates >100 μm |
| pH | | 5.17 |
| Viscosity data | Haake ($4 s^{-1}/20 s^{-1}/100 s^{-1}$) | 125/196/321 |
| | Brookfield RVDVII+ (S28; 5 rpm) | 98 300 cP |

| | | T + 1 month |
|---|---|---|
| Macroscopic appearance | RT | Identical to T0 |
| Microscopic appearance | RT | Identical to T0 |
| pH | RT | 4.95 |
| Haake rheology ($4 s^{-1}/20 s^{-1}/100 s^{-1}$) | | 117/171/310 |
| Brookfield RVDVII+ (S29; 5 rpm) | | 81 800 cP |

Chemical Stability:

Adapalene:

| Stability conditions | | Time | |
|---|---|---|---|
| | | T0 | T + 1 month |
| RT | g/g | 0.098 | 0.098 |
| | % of theoretical titre | 98 | 98 |

Benzoyl Peroxide:

| Stability conditions | | Time | |
|---|---|---|---|
| | | T0 | T + 1 month |
| RT | g/g | 2.484 | 2.436 |
| | % of theoretical titre | 99 | 97 |

Example 13

Formulation of Cream Type Containing 0.1% Adapalene, 2.5% Benzoyl Peroxide, and 2% Dermacryl 79 as Film-Forming Agent The composition is formulated according to the procedure described by the main and/or alternative process.

Constituents Content (% w/w):

| Benzoyl peroxide | 2.50 |
|---|---|
| Adapalene | 0.10 |
| Propylene glycol | 6.00 |
| Synperonic PE/L44 | 0.20 |
| EDTA | 0.10 |
| Glycerol | 7.00 |
| Natrosol HHX250 | 0.20 |
| Eumulgin B2 PH | 3.00 |
| Speziol C18 pharma | 2.00 |
| Miglyol 812 N | 7.00 |
| Arlacel 165 FL | 3.00 |
| ST-Cyclomethicone 5NF | 6.00 |
| Simulgel 600PHA | 2.00 |
| Dermacryl 79 | 2.00 |
| Purified water | qs 100% |
| Triethanolamine | qs pH 5.5 ± 0.5 |

Stability Data:
Physical Stability:

| Characterization at T0 | | |
|---|---|---|
| Macroscopic appearance | | White cream |
| Microscopic appearance | | Dispersion of the active agents without aggregates >100 μm |
| pH | | 5.51 |
| Viscosity data | Haake ($4\,s^{-1}/20\,s^{-1}/100\,s^{-1}$) | 109/156/267 |
| | Brookfield RVDVII+ (S28; 5 rpm) | 70 000 cP |

| | | T + 1 month |
|---|---|---|
| Macroscopic appearance | RT | Identical to T0 |
| Microscopic appearance | RT | Identical to T0 |
| pH | RT | 5.55 |
| Haake rheology ($4\,s^{-1}/20\,s^{-1}/100\,s^{-1}$) | | 84/132/232 |
| Brookfield RVDVII+ (S29; 5 rpm) | | 114 000 cP |

Chemical Stability:
Adapalene:

| | | Time | |
|---|---|---|---|
| Stability conditions | | T0 | T + 1 month |
| RT | g/g | 0.098 | 0.096 |
| | % of theoretical titre | 98 | 96 |

Benzoyl Peroxide:

| | | Time | |
|---|---|---|---|
| Stability conditions | | T0 | T + 1 month |
| RT | g/g | 2.442 | 2.453 |
| | % of theoretical titre | 98 | 98 |

Example 14

Formulation of Lotion Type Containing 0.3% Adapalene, 1.0% Benzoyl Peroxide, and 3% Kollidon 90F as Film-Forming Agent The composition is formulated according to the procedure described by the main and/or alternative process.
Constituents Content (% w/w):

| | |
|---|---|
| Benzoyl peroxide | 1.00 |
| Adapalene | 0.30 |
| Avicel CL611 | 1.50 |
| Synperonic PE/L44 | 0.20 |
| Methyl paraben | 0.15 |
| Brij 721 | 3.00 |
| Arlacel 1656FL | 3.00 |
| Propyl paraben | 0.05 |
| Sophiderm | 5.00 |
| Cetiol SN PH | 5.00 |
| Dipropylene glycol | 3.00 |
| Simulgel 600PHA | 1.00 |
| Kollidon 90F | 3.00 |
| Purified water | qs 100% |

Stability Data:
Physical stability:

| Characterization at T0 | | |
|---|---|---|
| Macroscopic appearance | | White lotion |
| Microscopic appearance | | Dispersion of the active agents without aggregates >100 μm |
| pH | | 6.10 |
| Viscosity data | Haake ($4\,s^{-1}/20\,s^{-1}/100\,s^{-1}$) | 34/70/158 |
| | Brookfield LVDVII+ (S64; 6 rpm) | 33 793 cP |

| | | T + 1 month |
|---|---|---|
| Macroscopic appearance | RT | Identical to T0 |
| Microscopic appearance | RT | Identical to T0 |
| pH | RT | 5.12 |
| Haake rheology ($4\,s^{-1}/20\,s^{-1}/100\,s^{-1}$) | | 33/57/129 |
| Brookfield RVDVII+ (S29; 5 rpm) | | 32 193 cP |

Chemical Stability:
Adapalene:

| | | Time | |
|---|---|---|---|
| Stability conditions | | T0 | T + 1 month |
| RT | g/g | 0.293 | 0.290 |
| | % of theoretical titre | 98 | 97 |

Benzoyl Peroxide:

| | | Time | |
|---|---|---|---|
| Stability conditions | | T0 | T + 1 month |
| RT | g/g | 0.976 | 0.989 |
| | % of theoretical titre | 98 | 99 |

Example 15

Formulation of Lotion Type Containing 0.3% Adapalene, 1% Benzoyl Peroxide, and 0.5% Sodium Hyaluronate as Film-Forming Agent The composition is formulated according to the procedure described by the main and/or alternative process.

Constituents Content (% w/w):

| | |
|---|---|
| Benzoyl peroxide | 1.00 |
| Adapalene | 0.30 |
| Avicel CL611 | 1.50 |
| Synperonic PE/L44 | 0.20 |
| Methyl paraben | 0.15 |
| Brij 721 | 3.00 |
| Arlacel 165FL | 3.00 |
| Propyl paraben | 0.05 |
| Sophiderm | 5.00 |
| Cetiol SN PH | 5.00 |
| Dipropylene glycol | 3.00 |
| Simulgel 600PHA | 1.50 |
| Sodium hyaluronate | 0.50 |
| Purified water | qs 100% |

Stability Data:

Physical Stability:

| Characterization at T0 | |
|---|---|
| Macroscopic appearance | White lotion |
| Microscopic appearance | Dispersion of the active agents without aggregates >100 μm |
| pH | 6.03 |
| Viscosity data | Haake ($4\ s^{-1}/20\ s^{-1}/100\ s^{-1}$) 53/92/139 |
| | Brookfield RVDVII+ (S31; 5 rpm) 30 528 cP |

| | | T + 1 month | T + 2 months | T + 3 months |
|---|---|---|---|---|
| Macroscopic appearance | RT | Identical to T0 | Identical to T0 | Identical to T0 |
| Microscopic appearance | RT | Identical to T0 | Identical to T0 | Identical to T0 |
| pH | RT | 5.17 | 5.00 | 4.82 |
| Haake rheology ($4\ s^{-1}/20\ s^{-1}/100\ s^{-1}$) | | 47/75/120 | 44/74/121 | 38/61/109 |
| Brookfield RVDVII+ (S31; 5 rpm) | | 25 664 cP | 22 336 cP | 21 312 cP |

Chemical Stability:

Adapalene:

| | | Time | | | |
|---|---|---|---|---|---|
| Stability conditions | | T0 | T + 1 month | T + 2 months | T + 3 months |
| RT | g/g | 0.286 | 0.285 | 0.285 | 0.306 |
| | % of theoretical titre | 95 | 95 | 95 | 102 |

Benzoyl Peroxide:

| | | Time | | | |
|---|---|---|---|---|---|
| Stability conditions | | T0 | T + 1 month | T + 2 months | T + 3 months |
| RT | g/g | 0.98 | 0.96 | 0.95 | 0.96 |
| | % of theoretical titre | 98 | 96 | 95 | 96 |

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A stable, topically applicable pharmaceutical/cosmetic composition non-irritant over the long term, comprising otherwise essentially incompatible amounts of at least one naphthoic acid compound and benzoyl peroxide, said naphthoic acid compound and said benzoyl peroxide being in dispersed form in said composition; and, providing degradation-resistance thereto, a thus effective amount of at least one film-forming agent, formulated into a topically applicable, physiologically acceptable medium therefor as a gel, lotion, cream or emulsifier-free cream, wherein the at least one film-forming agent is at least one filmy forming polymer selected from the group consisting of polyvinylpyrrolidones, polysaccharides other than cellulose and derivatives thereof, acrylic copolymers and polyvinyl alcohols, said composition excluding ethyl alcohol, said pharmaceutical/cosmetic composition comprising, from 0.1% to 0.3% of 6-[3-(1-adamantyl)-4-methoxyphenyl]-2-naphthoic acid as the naphthoic acid;
from 1% to 10% of benzoyl peroxide;
from 30% to 95% of water;
from 0.5% to 10% of the at least one film-forming polymer;
from 0.10% to 3% of one or more gelling agents and/or suspending agents and/or pH-independent gelling agents;
from 0% to 1.5% of one or more chelating agents;
from 0.1% to 10% of one or more wetting agents; and
from 0.01% to 3% of preservatives.

2. The stable pharmaceutical/cosmetic composition as defined by claim 1, wherein said at least one film-forming polymer is a water-soluble polyvinylpyrrolidone.

3. The stable pharmaceutical/cosmetic composition as defined by Claim 1, wherein said at least one film-forming polymer is selected from the group consisting of a pectin, a gum and sodium hyaluronate.

4. The stable pharmaceutical/cosmetic composition as defined by claim 1, wherein said at least one film-forming polymer is an acrylic copolymer selected from the group consisting of acrylates/dimethylaminoethyl methacrylate copolymers, acrylates/ammonium methacrylate copolymers and acrylates/octylacrylamide copolymers.

5. The stable pharmaceutical/cosmetic composition as defined by claim 1, wherein said at least one film-forming polymer is a polyvinyl alcohol selected from among those polyvinyl alcohols having a degree of polymerization ranging from 500 to 5,000, a degree of hydrolysis ranging from 85 to 89% and a viscosity ranging from 20 to 65 mPa·s (4% (w/w) in water at 20° C.).

6. The stable pharmaceutical/cosmetic composition as defined by claim 1, wherein the concentration of said 6-[3-(1-adamantyl)-4-methoxyphenyl]-2-naphthoic acid is approximately 0.1% by weight relative to the total weight thereof.

7. The stable pharmaceutical/cosmetic composition as defined by claim 1, wherein the concentration of said 6-[3-(1-adamantyl)-4-methoxyphenyl]-2-naphthoic acid is approximately 0.3% by weight relative to the total weight thereof.

8. The stable pharmaceutical/cosmetic composition as defined by claim 1, wherein the concentration of said at least one film-forming polymer is 0.5%, 1%, 2%, 3%, 4% or 6% by weight of the total weight thereof.

9. The stable pharmaceutical/cosmetic composition as defined by claim 1, in the form of an aqueous, aqueous-alcoholic or oily dispersion, an aqueous, anhydrous or lipophilic gel, an emulsion of liquid or semi-liquid consistency obtained by dispersing a fatty phase in an aqueous phase or vice versa, or a suspension of soft or semi-liquid consistency, or a microemulsion, microcapsules, microparticles or vesicular dispersions of ionic and/or nonionic type.

10. The stable pharmaceutical/cosmetic composition as defined by claim 9, in the form of a gel.

11. The stable pharmaceutical/cosmetic composition as defined by claim 9, in the form of an emulsion.

12. The stable pharmaceutical/cosmetic composition as defined by claim 11, wherein the emulsion is in a form of a lotion, a cream or an emulsifier-free cream.

13. The stable pharmaceutical/cosmetic composition as defined by claim 9, comprising, in water:
from 0.1% to 0.3% of the naphthoic acid compound;
from 2% to 5% of benzoyl peroxide;
from 30% to 95% of water;
from 1% to 10% of at least one film-forming polymer;
from 0.1% to 3% of one or more gelling agents and/or suspending agents and/or pH-independent gelling agents;
from 0.01% to 1.5% of chelating agents;
from 0.1% to 10% of one or more wetting agents;
from 0.1% to 20% of an emollient; and
from 0.01% to 3% of preservatives.

14. The stable pharmaceutical/cosmetic composition as defined by claim 9, comprising, in water:
from 0.1% to 0.3% of the naphthoic acid compound;
from 2% to 5% of benzoyl peroxide;
from 30% to 95% of water;
from 0.5% to 10% of at least one film-forming polymer;
from 0.1% to 3% of one or more gelling agents and/or suspending agents and/or pH-independent gelling agents;
from 0% to 1.5% of one or more chelating agents;
from 0.1% to 10% of one or more wetting agents;
from 0% to 20% of one or more humectants and/or emollients;
from 0% to 10% of emulsifiers;
from 0.1% to 30% of fatty phase; and
from 0% to 20% of one or more additives.

15. The stable pharmaceutical/cosmetic composition as defined by claim 1, formulated as a medicament.

16. A process for formulating a composition as defined by claim 1, comprising the following steps:
a) preparing an active phase 1 comprising one of the two active agents;
b) preparing an active phase 2 comprising the other active agent;
c) preparing an aqueous phase;
d) optionally preparing a film-forming phase;
e) mixing of the 2 active phases prepared in a) and b);
f) optionally preparing a fatty phase;
g) optionally emulsifying the mixture of phases obtained in f) and c);
h) mixing of the phase obtained in g) or c) with the single active phase obtained in e);
i) optionally adding polyacrylamide;
j) optionally neutralizing the formulation obtained in h);
k) optionally adding the film-forming phase;
l) optionally adjusting with water.

17. The process as defined by claim 16, wherein the active ingredients are mixed in the $1^{st}$ step of the process; thus, steps a) and b) are replaced with step a'):
a') preparing a single active phase comprising the two active agents; and continuing as described starting from step c).

18. A process as defined by claim 16, comprising the following steps:
Step a: Preparation of active phase 1;
Mixing purified water and active ingredient 1 (adapalene) with at least one wetting agent until said naphthoic acid compound is completely dispersed, to obtain active phase 1;
Step b: Preparation of active phase 2;
Mixing purified water and active ingredient 2 (benzoyl peroxide) with at least one wetting agent until said benzoyl peroxide is completely dispersed, to obtain active phase 2;
Step c: Preparation of the aqueous phase:
Introducing into a beaker, with stirring, if necessary at high temperature, purified water and the gelling agent(s) and/or pH-independent gelling agent(s) other than polyacrylamide and/or suspending agent(s) and optionally the chelating agent(s), the preservative(s), the hydrophilic emulsifier(s), the stabilizer(s), the humectant(s) and/or emollient(s), and the film-forming polymer(s);
Step d: Optionally; mixing at least one film-forming polymer with water to obtain a film-forming phase;
Step e: Mixing of the active phases:
Mixing the two active phases obtained respectively in a) and b); and maintaining the stirring until complete homogenization;
Step f (optionally for obtaining an emulsion): Preparation of the fatty phase:
Mixing of the oily compounds, of the solid fatty substances and optionally of the lipophilic emulsifiers and the preservatives;
Heating the mixture and after homogenization the volatile silicone is introduced last, if present in the composition;
Step g (optional): Emulsification:
Introducing at high temperature the fatty phase into the aqueous phase to carry out the emulsification, and maintaining the for a few minutes, then cooling the product;
Step h: Addition of the single active phase:
Introducing the single active phase obtained in e) into the aqueous phase obtained in c) for gels or into the phase obtained in g) for emulsions;
Step i (optional): Addition of polyacrylamide:
Introducing polyacrylamide, with stirring, into the phase obtained in h); the stirring is maintained until complete homogenization;

Step j: Neutralization:

The neutralizing agent for the gelling agent is introduced, if necessary, into the phase obtained in h) or i);

Step k: (optional) Addition of the film-forming phase:

Adding the film-forming phase prepared in step d) if the film-forming polymer(s) have not been introduced into the aqueous phase; and Step l: (optional) Adjustment with water:

If necessary, adjusting with water.

19. The process as defined by claim 18, wherein the active ingredients are mixed in the $1^{st}$ step of the process; thus, steps a) and b) are replaced with step a'):

a') preparing a single active phase comprising the two active agents; and continuing as described starting from step c).

20. A method for the treatment of a dermatological condition associated with a keratinization disorder related to cell differentiation and proliferation, comprising administering to an individual in need of such treatment, for such period of time as required to elicit the desired effect, a thus effective amount of the stable pharmaceutical/cosmetic composition as defined by claim 1.

21. The method as defined by claim 20, for the treatment of a dermatological condition associated with a keratinization disorder relating to cell differentiation and proliferation selected from the group consisting of acne vulgaris, comedonal acne, papulopustular acne, papulocomedonal acne, nodulocystic acne, acne conglobata, acne keloid of the nape of the neck, recurrent miliary acne, acne necrotica, acne neonatorum, occupational acne, acne rosacea, senile acne, solar acne and acne medicamentosa.

22. The method as defined by claim 21, comprising the treatment of acne vulgaris.

23. A method for the treatment of acne-prone skin, for combating the greasy appearance of the skin or the hair, for protecting against the harmful effects of sunlight, or for the treatment of physiologically greasy skin, or for treating signs of photo-induced or chronological aging, comprising administering to an individual in need of such treatment, for such period of time as required to elicit the desired effect, a thus effective amount of the stable pharmaceutical/cosmetic composition as defined by claim 1.

24. The gel of claim 10, comprising one or more of the following ingredients:

a) one or more emollients and/or humectants; and b) one or more additives.

25. The emulsion of claim 11, comprising one or more of the following ingredients:

a) one or more emollients and/or humectants;

b) one or more emulsifiers; and c) one or more additives.

26. The stable pharmaceutical/cosmetic composition as defined by claim 1, wherein the concentration of said benzoyl peroxide is from 2% to 7% by weight relative to the total weight thereof.

27. The stable pharmaceutical/cosmetic composition as defined by claim 4, wherein the concentration of said benzoyl peroxide is from 2.5% to 5% by weight relative to the total weight thereof.

28. The stable pharmaceutical/cosmetic composition as defined by claim 7, wherein the concentration of said benzoyl peroxide is from 2.5% to 5% by weight relative to the total weight thereof.

29. The stable pharmaceutical/cosmetic composition as defined by claim 1, wherein said at least one film-forming polymer is a polyvinyl alcohol.

\* \* \* \* \*